(12) United States Patent
Bauerfeind

(10) Patent No.: US 12,232,994 B2
(45) Date of Patent: Feb. 25, 2025

(54) STABILIZING ROD FOR AN ORTHOPAEDIC AID

(71) Applicant: Bauerfeind AG, Zeulenroda-Triebes (DE)

(72) Inventor: Hans B. Bauerfeind, Zeulenroda-Triebes (DE)

(73) Assignee: Bauerfeind AG, Zeulenroda-Triebes (DE)

( * ) Notice: Subject to any disclaimer, the term of this patent is extended or adjusted under 35 U.S.C. 154(b) by 0 days.

(21) Appl. No.: 17/055,909

(22) PCT Filed: May 17, 2019

(86) PCT No.: PCT/EP2019/062833
§ 371 (c)(1),
(2) Date: Nov. 16, 2020

(87) PCT Pub. No.: WO2019/219925
PCT Pub. Date: Nov. 21, 2019

(65) Prior Publication Data
US 2021/0186734 A1    Jun. 24, 2021

(30) Foreign Application Priority Data

May 17, 2018   (DE) ............... 10 2018 207 727.4

(51) Int. Cl.
*A61F 5/01* (2006.01)
(52) U.S. Cl.
CPC .... *A61F 5/0109* (2013.01); *A61F 2005/0179* (2013.01)

(58) Field of Classification Search
CPC ........ A61F 5/0109; A61F 5/01; A61F 5/3707; A61F 5/0118; A61F 5/0106; A61F 5/0123; A61F 5/012; A61F 2005/0179; A61F 2005/0137
USPC .......................................... 602/26
See application file for complete search history.

(56) References Cited

U.S. PATENT DOCUMENTS

| 750,903 | A | * | 2/1904 | Schrum et al. | ....... B21F 27/005 |
| | | | | | 256/45 |
| 952,088 | A | * | 3/1910 | Wilson | .............................. 2/264 |
| 1,188,355 | A | * | 6/1916 | Schuler | .................... A41C 1/16 |
| | | | | | 2/264 |

(Continued)

FOREIGN PATENT DOCUMENTS

| CN | 105996224 A | 10/2016 |
| DE | 4412765 A1 | 10/1995 |

(Continued)

OTHER PUBLICATIONS

English translation of International Preliminary Report on Patentability for PCT/EP2019/062833 dated Nov. 17, 2020, 9 pages.

(Continued)

*Primary Examiner* — Ophelia A Hawthorne
*Assistant Examiner* — Michael Milo
(74) *Attorney, Agent, or Firm* — Sheppard Mullin Richter & Hampton LLP

(57) ABSTRACT

The invention relates to a stabilizing rod (99, 101) for an orthopedic aid, the stabilizing rod (99, 101) having a bending section (130) in the longitudinal direction, the bending section (130) having at least one mesh belt structure (131).

14 Claims, 5 Drawing Sheets

(56) References Cited

U.S. PATENT DOCUMENTS

| | | | |
|---|---|---|---|
| 5,733,249 A * | 3/1998 | Katzin | A61F 5/0106 602/21 |
| 6,149,616 A | 11/2000 | Szlema et al. | |
| 7,534,220 B2 | 5/2009 | Cormier et al. | |
| 8,784,349 B1 * | 7/2014 | Nelson | A61F 5/0109 602/61 |
| 9,314,363 B2 | 4/2016 | Ingimundarson et al. | |
| 9,795,500 B2 | 10/2017 | Ingimundarson et al. | |
| 2003/0204156 A1 | 10/2003 | Nelson et al. | |
| 2005/0070831 A1 | 3/2005 | Cormier et al. | |
| 2006/0142682 A1 | 6/2006 | Hassler et al. | |
| 2007/0106191 A1 | 5/2007 | Mueller et al. | |
| 2007/0167891 A1 | 7/2007 | Gramza et al. | |
| 2009/0144873 A1 | 6/2009 | Jewell et al. | |
| 2012/0004584 A1 | 1/2012 | Chiang | |
| 2012/0109031 A1 | 5/2012 | Vollbrecht et al. | |
| 2013/0053743 A1 * | 2/2013 | Reinhardt | A61F 13/061 602/26 |
| 2013/0110023 A1 | 5/2013 | Scheuermann et al. | |
| 2015/0290012 A1 | 10/2015 | Ferrigolo et al. | |
| 2017/0297278 A1 * | 10/2017 | LeCursi | B29C 70/28 |
| 2017/0318872 A1 | 11/2017 | Fillis | |
| 2021/0236319 A1 * | 8/2021 | Teng | A61F 5/01 |

FOREIGN PATENT DOCUMENTS

| | | | |
|---|---|---|---|
| EP | 0970668 A1 | 1/2000 | |
| WO | 2011035885 A1 | 3/2011 | |
| WO | WO 2018087122 A1 * | 11/2016 | A61F 5/026 |
| WO | WO 2017/055222 A2 | 4/2017 | |

OTHER PUBLICATIONS

International Search Report and Written Opinion for PCT/EP2019/062833, dated Jul. 25, 2019, with English translation of ISR, 11 pages.

* cited by examiner

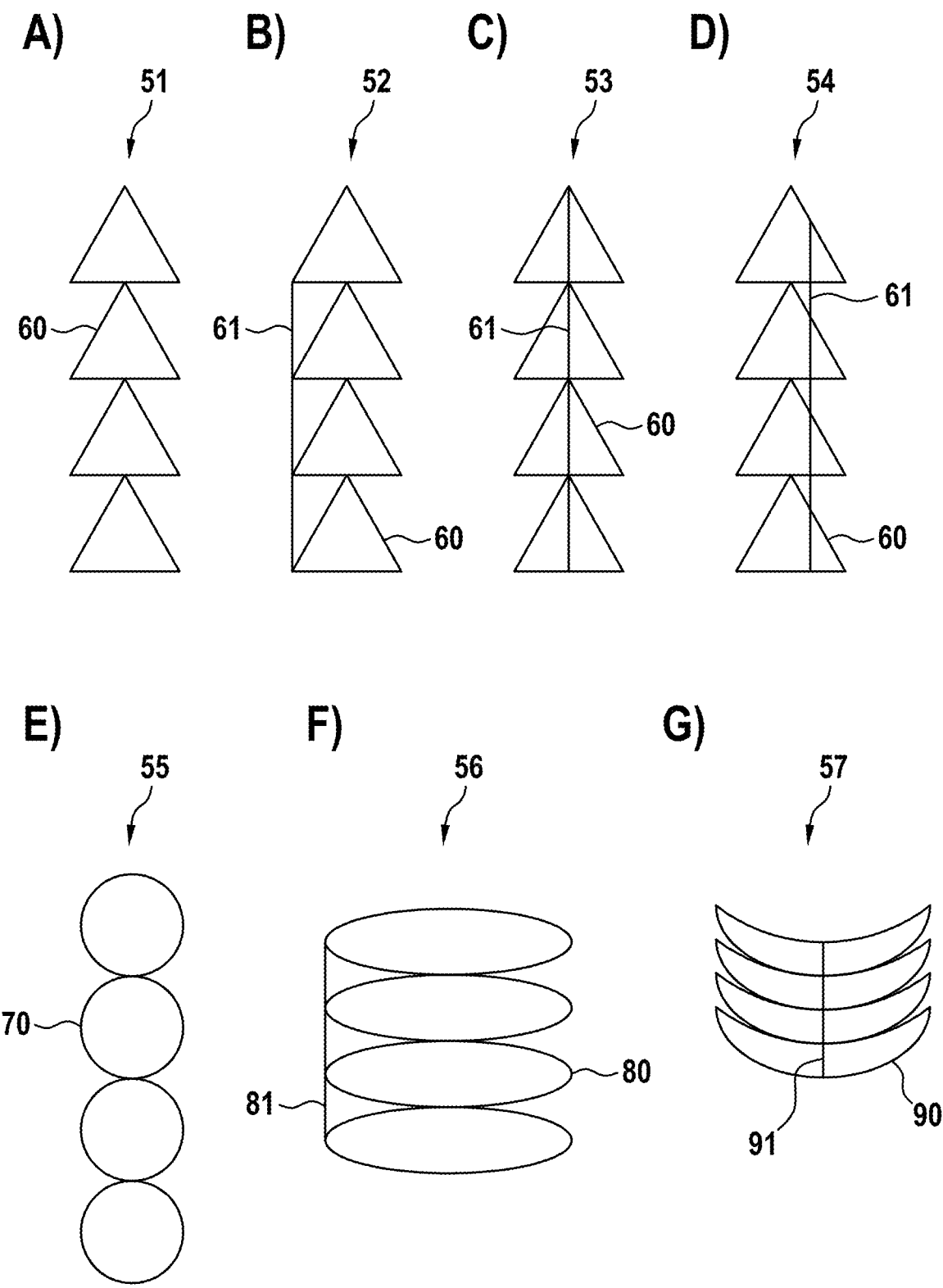

STABILIZING ROD FOR AN ORTHOPAEDIC AID

CROSS REFERENCE TO RELATED APPLICATIONS

This application is a U.S. National Stage Application under 35 U.S.C. 371 of International Application No. PCT/EP2019/062833, filed May 17, 2019, which claims priority to German Patent Application 10 2018 207 727.4, filed May 17, 2018. The contents of each of the aforementioned are hereby incorporated by reference in their entirety into the present disclosure.

The present invention relates to stabilizing rods for an orthopedic aid, particularly knee bandages and orthopedic aids, comprising at least one stabilizing rod according to the invention.

The use of stabilizing rods in orthopedic aids is known. Knee joint bandages, knee bandages for short, with lateral stabilizing rods are known from WO 2011/035885 A1 and DE 3637 879 A1. In this case, stabilizing rods are used which are made of metal and are bendable as a result of their structure as spring band rods, i.e. flat-pressed coils of a helical spring. However, since such stabilizing rods are often welded to the textile of the orthopedic aid, at least partial regions of the metallic spring band rods must be laminated with a weldable plastic. In addition, the metal can destroy the adjacent textile. The flat spiral springs used are equally elastic over the entire course of the spring and the degree of inflection cannot be limited.

The technical problem addressed by the present invention is that of providing improved stabilizing rods for an orthopedic aid, particularly knee bandages, which function at least as well as the stabilizing rods from the prior art, but can be produced in a simpler and less expensive manner, can be easily welded, are lighter and/or protect the adjacent textile.

The present invention solves this technical problem by means of a stabilizing rod according to claim 1.

In particular, the present invention solves the technical problem addressed by means of a stabilizing rod for an orthopedic aid, particularly a knee bandage, the stabilizing rod having a bending section, the bending section having a mesh belt structure.

The bending section preferably has at least one mesh belt structure.

The mesh belt structure preferably extends over the length of the stabilizing rod.

In connection with the present invention, a mesh belt structure refers to a mesh belt or the mesh belt, i.e., a mesh-shaped structure with gaps. The mesh belt structure preferably has a polygonal, particularly diamond-shaped or rhombic structure, i.e., the gaps formed by the mesh are diamond-shaped or rhombic, for example, honeycomb-shaped.

However, other shapes are also possible, for example, rectangular, round, oval, elliptical, triangular, hexagonal, octagonal, or polygonal.

In the case of an angular shape of the individual structural elements of the mesh belt structure, particularly in the case of a diamond-shaped or rhombic structure, the angle of the corners is freely selectable. By selecting the angle size, the flexibility of the stabilizing rod can be influenced in an advantageous manner. For example, the corners can have an angle of at least 30° and maximally 55° in the preferential direction of the deformation of the stabilizing rod.

Particularly in the case of a rhombus shape, two opposite corners preferably have the same angle, but two adjacent corners have a different angle. In such case, the difference between the angles can be at least 0.5°.

In connection with the present invention, the angle of a corner refers to the angle which is present at the corner in the not elongated, unstretched and unbent state.

Particularly in the case of rhombic or triangular structures, one corner or two or more corners can be designed as a hinge, i.e., so bendable that the angle of the corner can be of a different size.

In a triangular embodiment of the structural elements, the hypotenuse of one triangle is preferably connected to the tip of another triangle.

The spring effect in a triangular embodiment of the structural elements is created by a convex or concave deformation of the hypotenuse. As a result of the deformation, the corners adjoining the hypotenuse approach one another, so that the structural element becomes narrower during the deformation.

In the case of a round embodiment of the structural elements, the radius can be selected freely, as can the area of curvature in the case of an oval or ellipsoidal embodiment of the structural elements.

The structural elements can also have an elongated shape, for example, be banana-shaped.

If the structure has particularly a thin bending rod next to or in the mesh belt structure or if more than one mesh belt structure is provided, the individual structural elements of the mesh belt structure are preferably triangular or square and/or have no more than four corners because, for example, hexagons or octagons are less bendable.

In the mesh belt structure according to the invention, a plurality of gaps formed by the mesh-shaped structure, i.e., the mesh, lie one behind the other in the longitudinal direction of the stabilizing rod. The mesh belt structure thus comprises a plurality of gaps which lie in a row and are formed by the mesh.

In a preferred embodiment, the stabilizing rod is designed as one piece. The stabilizing rod preferably consists of a single material, particularly a plastic. However, the stabilizing rod can also consist of several materials, for example, several plastics or of a base material and a coating.

However, the stabilizing rod can also consist of several materials, for example, several plastics. The gaps formed by the mesh belt structure can also be filled with a further material, particularly a softer material, for example, a foam. This can also influence the flexibility of the stabilizing rod.

The flexibility of the corresponding section or of the entire stabilizing rod can also be adjusted in an advantageous manner with the selection of the size of the gaps. The flexibility can also be influenced by the ratio and the graduation of the interior angles of the preferably rhombic gaps.

The length and positioning of the bending section can also advantageously determine the position and strength of the flexibility of the stabilizing rod.

Another possibility of adjusting the flexibility results from the selection of the thickness and the cross section of an optional thin bending rod.

The stabilizing rod preferably comprises a thin bending rod and at least one mesh belt structure. The stabilizing rod is preferably formed from a thin bending rod and at least one mesh belt structure. The thin bending rod can lie on the edge of the mesh belt structure or pass through the mesh belt structure in the center or off-center.

In a particular embodiment, the thin bending rod can have a guide, for example, a guide channel. For example, the thin bending rod can be hollow, particularly designed as a tube.

As a result, a cord or the like can be guided in the rod or a core can be located in the rod, for example, a metal core, which increases the stability of the stabilizing rod or strengthens its spring force.

The bending section of the stabilizing rod, particularly the stabilizing rod, is preferably formed from a thin bending rod and at least one mesh belt structure running on said rod.

The bending section of the stabilizing rod, particularly the stabilizing rod, is preferably formed from a thin bending rod and one mesh belt structure running on said rod.

However, the stabilizing rod can also have a plurality of mesh belt structures, for example, two or three mesh belt structures. In particular, the stabilizing rod can have a plurality of, for example, two, mesh belt structures arranged next to one another, so that a plurality of, for example, two, rows of gaps formed by meshes extend in the longitudinal direction of the stabilizing rod.

The bending section of the stabilizing rod, particularly the stabilizing rod, is therefore also preferably formed from two mesh belt structures.

The bending section of the stabilizing rod, particularly the stabilizing rod, is therefore preferably formed from two mesh belt structures and a thin bending rod running between them.

Alternatively, the bending section of the stabilizing rod is formed without a thin bending rod and only from at least one mesh belt structure. The bending section of the stabilizing rod is preferably formed without a thin bending rod and only from one mesh belt structure. The bending section of the stabilizing rod is preferably formed without a thin bending rod and only from at least two, preferably two, mesh belt structures. A stabilizing rod is preferred, in which one, particularly rhombic, mesh belt structure or two parallel, particularly rhombic, mesh belt structures extend over the length of the stabilizing rod.

A stabilizing rod is preferred, in which two parallel, particularly rhombic, mesh belt structures extend over the length of the stabilizing rod and a thin bending rod runs between said mesh belt structures.

In particular, four alternative preferred embodiments of the bending section of the stabilizing rod are thus described: 1. A mesh belt without a thin bending rod. 2. A mesh belt with an associated thin bending rod. 3. At least two mesh belts, particularly two mesh belts without a thin bending rod. 4. At least two mesh belts, particularly two mesh belts with an associated thin bending rod.

Surprisingly, it was also found that good and sufficient flexibility of the stabilizing rod can be achieved by a mesh belt structure without the stabilizing rod having to be designed as a spring band rod. Since no spring band rod, particularly a continuous spring band rod, is necessary, metal and/or the circularly overlapping spring band can advantageously be omitted, resulting in the stabilizing rod protecting the adjacent textile. Advantageously, the stabilizing rod can also be produced in one piece and from plastic. By omitting a metal spring band rod, both the risk of breaking the rod with the associated risk of injury from sharp-edged pieces of metal and the possible generation of noise, such as creaking or squeaking, are reduced. Rust caused by sweat can also be prevented. The stabilizing rod according to the invention is also particularly light due to the mesh belt structure and the preferred configuration with plastic. A preferred plastic is a thermoplastic material, for example, polyurethane (TPU). The stabilizing rod can be produced in an advantageous and simple manner by injection molding.

The bending section of the stabilizing rod can be determined by the position of the bending section along the length of the stabilizing rod.

If the bending section preferably extends over the entire length of the stabilizing rod, the bending, or particularly bending, section of the stabilizing rod can be determined by the material thickness of the respective sections, in that the particularly bending section has a smaller material thickness. Alternatively or additionally, the flexibility in this region can also be increased by a different ratio of the interior angles of the gaps, particularly in the case of rhombic gaps.

In a preferred embodiment, the stabilizing rod is designed as one piece. In a preferred embodiment, the stabilizing rod consists of a single material. In a preferred embodiment, the stabilizing rod consists of a plastic, also of a rubber-like plastic.

Suitable plastics are known to a person skilled in the art, for example, thermoplastic polyurethane (TPU), polypropylene (PP), or polyethylene (PE). However, it is also possible to use rigid materials, for example, for defining a preferential direction or for configuring a hinge.

Different materials can also be combined, for example, a rod made of a rigid material, wherein the corners of the structural elements are formed from the more bendable thermoplastic polyurethane.

The base material can also be coated, for example, in order to achieve better adhesion of the rod to the bandage material.

The stabilizing rod is preferably barely expandable and/or compressible, particularly in the longitudinal direction, particularly if the preferred thin and bending rod is present.

The first and/or the second section of the stabilizing rod, particularly the first section of the stabilizing rod, preferably has a gripping piece. The gripping piece is preferably designed as an eyelet. The eyelet preferably has a bulge on its side facing away from the stabilizing rod. As an alternative to an eyelet, the at least one gripping piece can also have knobs on the stabilizing rod, which make it easier to grip the rod during application and removal.

In this case, the stabilizing rod is used with a double effect, namely for stabilizing the knee joint and as a slip-on and slip-off aid, for which the stabilizing rod is provided with at least one gripping piece which is easy to grip and transfers an exerted pull directly to the bandage material. It can be formed at the upper and/or lower end of the stabilizing rod. When the gripping piece is pulled, the stabilizing rod is thus introduced into the bandage over the entire length of said bandage. The gripping piece is expediently designed as an eyelet, in which the passage through its hole lies approximately at right angles to the bandage material. With such a design of the gripping piece, it can be gripped directly with one finger which passes through the eyelet and in this way conveniently transfers the pull to the bandage. The gripping of the eyelet can furthermore be facilitated, in that it has a bulge on its side facing away from the stabilizing rod. This makes it easier to grip the bandage with the fingers when applying or removing the bandage.

Surprisingly, it was found that the stabilizing rod, despite the mesh belt structure, is still stable enough to be also used as a slip-on aid.

The stabilizing rod according to the invention is preferably a stabilizing rod for a bandage. The stabilizing rod according to the invention is preferably a stabilizing rod for a knee joint bandage.

The present invention also relates to the use of a stabilizing rod according to the invention in an orthopedic aid, particularly a bandage, preferably a knee joint bandage, comprising a stabilizing rod according to one of the previous claims.

The present invention also relates to an orthopedic aid comprising a stabilizing rod according to the invention. The orthopedic aid is preferably a bandage. The orthopedic aid is particularly preferably a knee bandage or a knee joint bandage. The main part of the knee bandage or knee joint bandage is preferably formed from a textile, particularly a knitted fabric. Suitable knee bandages or knee joint bandages and their main parts are known to a person skilled in the art.

The present invention therefore also relates to a knee joint bandage comprising a stabilizing rod according to the invention.

A knee joint bandage is preferred, wherein the bending section of the stabilizing rod is located at the level of the knee when the knee joint bandage is in the applied state.

The knee joint bandage preferably has two stabilizing rods, particularly two stabilizing rods according to the invention.

A knee joint bandage is preferred, wherein the knee joint bandage has two stabilizing rods, particularly two stabilizing rods according to the invention, wherein the stabilizing rods extend over the length of the knee joint bandage. The stabilizing rods preferably extend at the side of the knee over the length of the knee joint bandage.

A knee joint bandage is preferred, wherein each of the bending sections of the stabilizing rods is located at the level of the knee when the knee joint bandage is in the applied state.

The at least one stabilizing rod is preferably embedded in a pocket arranged on the bandage. A partial region of the at least one stabilizing rod is preferably welded to the textile of the bandage and/or the pocket.

Preferred is a bandage, particularly a knee joint bandage, made of elastic material, particularly a textile, which is provided on at least one side with a stabilizing rod according to the invention extending over the length of the bandage, wherein the stabilizing rod is provided with one or two gripping pieces and is embedded in a pocket arranged on the bandage, which is firmly connected to the material of the bandage via edge zones and its end arranged above the kneecap. The stabilizing rod is preferably welded essentially continuously to the material of the bandage or is entirely or partially interlockingly connected to the material of the bandage via a pocket or via at least one eyelet or loop. The gripping piece is preferably designed as an eyelet, in which the passage through its hole lies approximately at right angles to the bandage material. The side facing away from the stabilizing rod preferably has a bulge.

The knee joint bandage preferably has a pad associated with the kneecap.

Further preferred embodiments are disclosed in the dependent claims, the examples and the drawings.

FIG. 5 shows different embodiments of the mesh belt structure.

FIG. 1 shows a stabilizing rod 99 according to the invention. The stabilizing rod 99 is designed as one piece and molded from a plastic.

Figure 1:
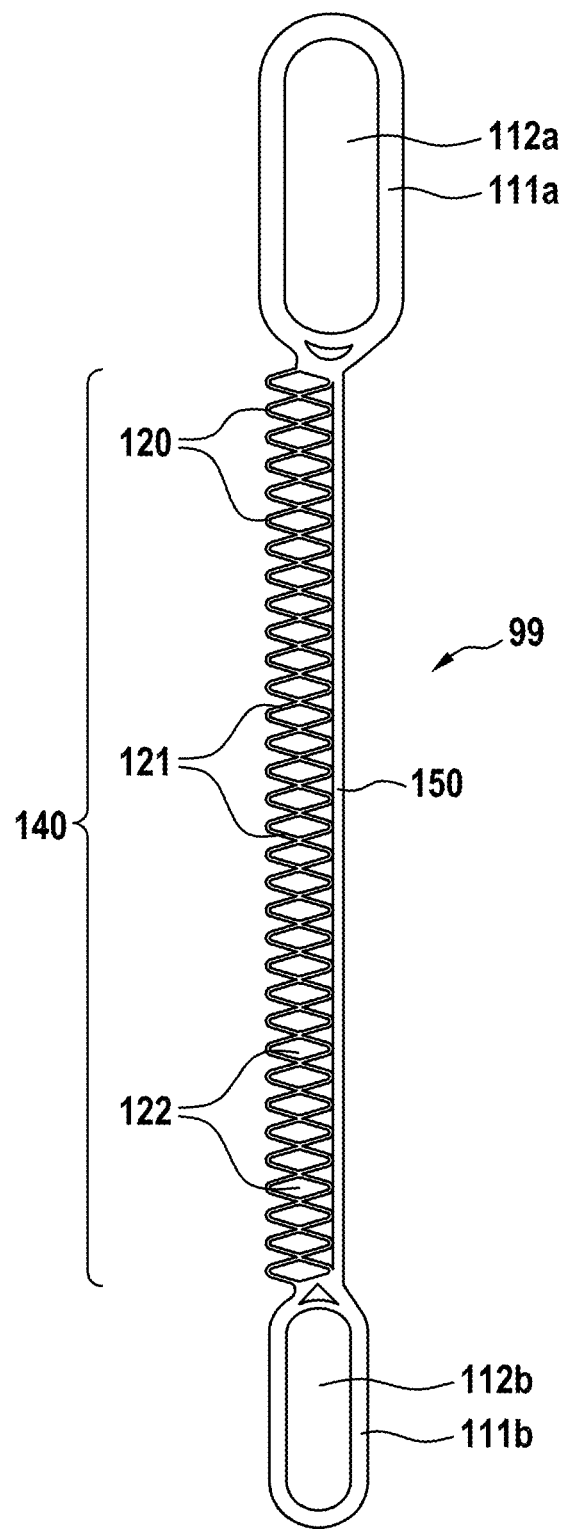
FIG. 1 shows a stabilizing rod according to the invention.

The bending section 140 of the stabilizing rod 99 is formed from a mesh belt structure 120 and a thin bending rod 150 lying on the mesh belt structure. The mesh belt structure 120 is formed from a mesh 121 which encloses rhombic gaps 122. Due to the mesh belt structure 120, the stabilizing rod 99 is bendable and light. The thin bending rod 150 restricts the stretchability or compressibility of the stabilizing rod 99 in the longitudinal direction, so that the stabilizing rod 99 can advantageously also be used as a slip-on and slip-off aid for an elastic bandage, for example, a knee bandage.

For this purpose, the stabilizing rod 99 has a gripping piece 111*a*/111*b* at each end, which form engagement holes 112*a*/112*b*. The gripping pieces 111*a*/111*b* are a component of the stabilizing rod 99 and are formed as one piece from the material of the stabilizing rod.

Figure 2:
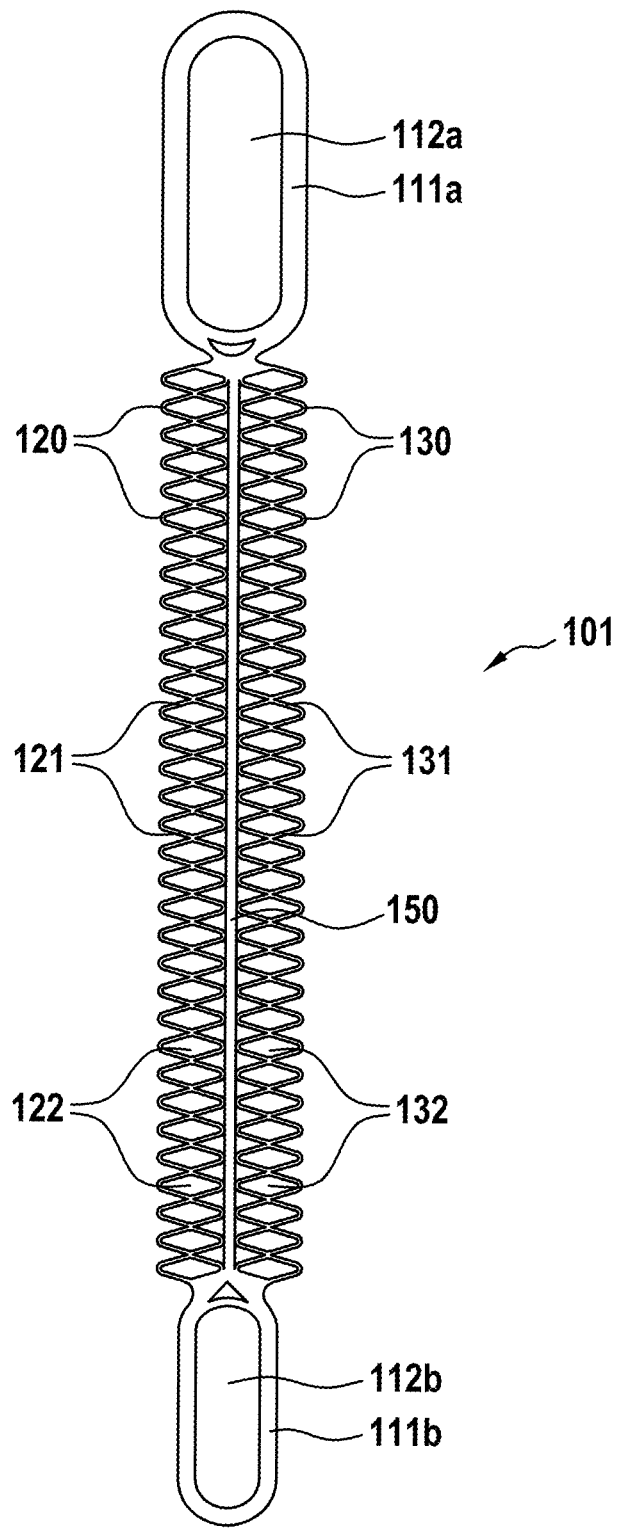
FIG. 2 shows an alternative embodiment of the stabilizing rod according to the invention.

FIG. 2 shows a further embodiment of a stabilizing rod 101 according to the invention. The stabilizing rod 101 is designed as one piece and molded from a plastic.

As in FIG. 1, the stabilizing rod 101 comprises a mesh belt structure 120 and a thin bending rod 150. In addition to the first mesh belt structure 120 with the mesh elements 121 and the rhombic gaps 122, the stabilizing rod 101 also has a second mesh belt structure 130, which also has rhombic gaps 132 formed by the meshes 131. The thin bending rod 150 runs between the two mesh belt structures 120/130. The thin bending rod 150 can, for example, also be hollow or have a guide channel for guiding a cord or a metal core through it.

In this embodiment, the stabilizing rod is wider but nevertheless easily bendable. At each end, the stabilizing rod 101 again has one gripping piece 111*a*/111*b*, each forming engagement holes 112*a*/*b*. The gripping pieces 111*a*/111*b* are a component of the stabilizing rod 101 and are formed as one piece from the material of the stabilizing rod.

Figure 3:
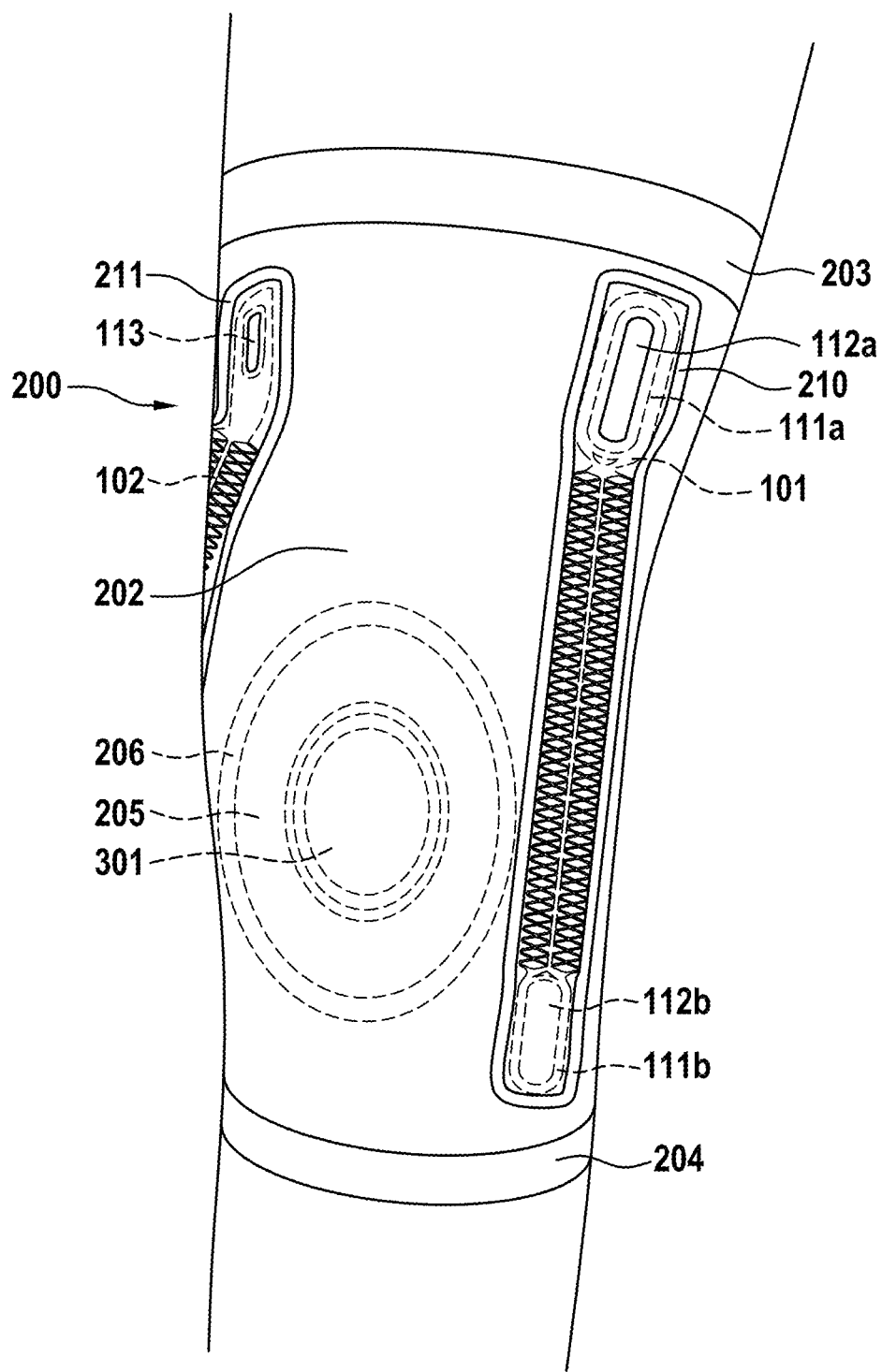
FIG. 3 shows a knee joint bandage according to the invention with two stabilizing rods from FIG. 2.

The knee joint bandage 200 shown in FIG. 3 consists of a stocking 202 made of elastic textile material, and it is provided with the two edges 203 and 204 at both ends, which help to prevent the bandage 200 from slipping. In addition, these edges 203 and 204 are made of a material that has a lower tension than the stocking 202 in order to only slightly constrict the leg of the wearer at the relevant points. On the front side of the knee joint, a profile insert is incorporated with the pad 205 into the stocking 202, which can consist, for example, of foam or silicone and which has considerable elasticity. The pad 205 is covered on the inside of the stocking 202 by a cover which is connected at its edges 206 to the stocking 202, for example, by gluing. In its central part, the pad 205 leaves a free region, into which the kneecap 301 fits. The kneecap 301 is thus encompassed by the pad 205. To this extent, it is a knee joint bandage designed in a known manner. In addition to the pad 205, the bandage 200 is provided with two stabilizing rods 101 and 102 according to the invention, which extend essentially over the entire length of the bandage 200 and which ensure that the bandage 200 applied to the leg cannot contract in terms of its longitudinal direction. These stabilizing rods 101 and 102 are stabilizing rods as shown in FIG. 2. Each of the two stabilizing rods 101 and 102 is received in a pocket glued to the bandage 200 by means of the edge zone 210 or 211 to the material of the bandage 200. Depending on the desired stabilization intensity, the bandage 200 can also be provided with only one stabilizing rod. Each of the two stabilizing rods 101 and 102 has at its ends a gripping piece 111*a*/111*b* containing an eyelet 112*a*/112*b* or 113, which allows for the bandage 200 to be gripped with the finger when it is put on and pulled up or taken off and pulled down along the leg, thus facilitating the putting on or taking off of the bandage 200 because, when the gripping pieces 111a/111b are pulled accordingly, the bandage 200 is carried along by said gripping pieces and the stabilizing rod 101, 102 as a whole, making is easily possible to pull the bandage 200 smoothly over the foot, the calf and the knee to its final position. The stabilizing rods 101 and 102 contained in the pockets are fully encompassed by the respective pockets, in that their edge zones 210 and 211 are each designed as a narrow continuous strip which is directly connected to the material of the bandage 200, for example, by welding or gluing.

The particular configuration of the stabilizing rods 101, 102 preferred according to the invention shall be described in greater detail in FIG. 2.

In this case, the bending section of the stabilizing rods 101, 102 is located at the level of the kneecap 301. Thus, when the knee is bent, precisely said bending section is also bent.

Figure 4:
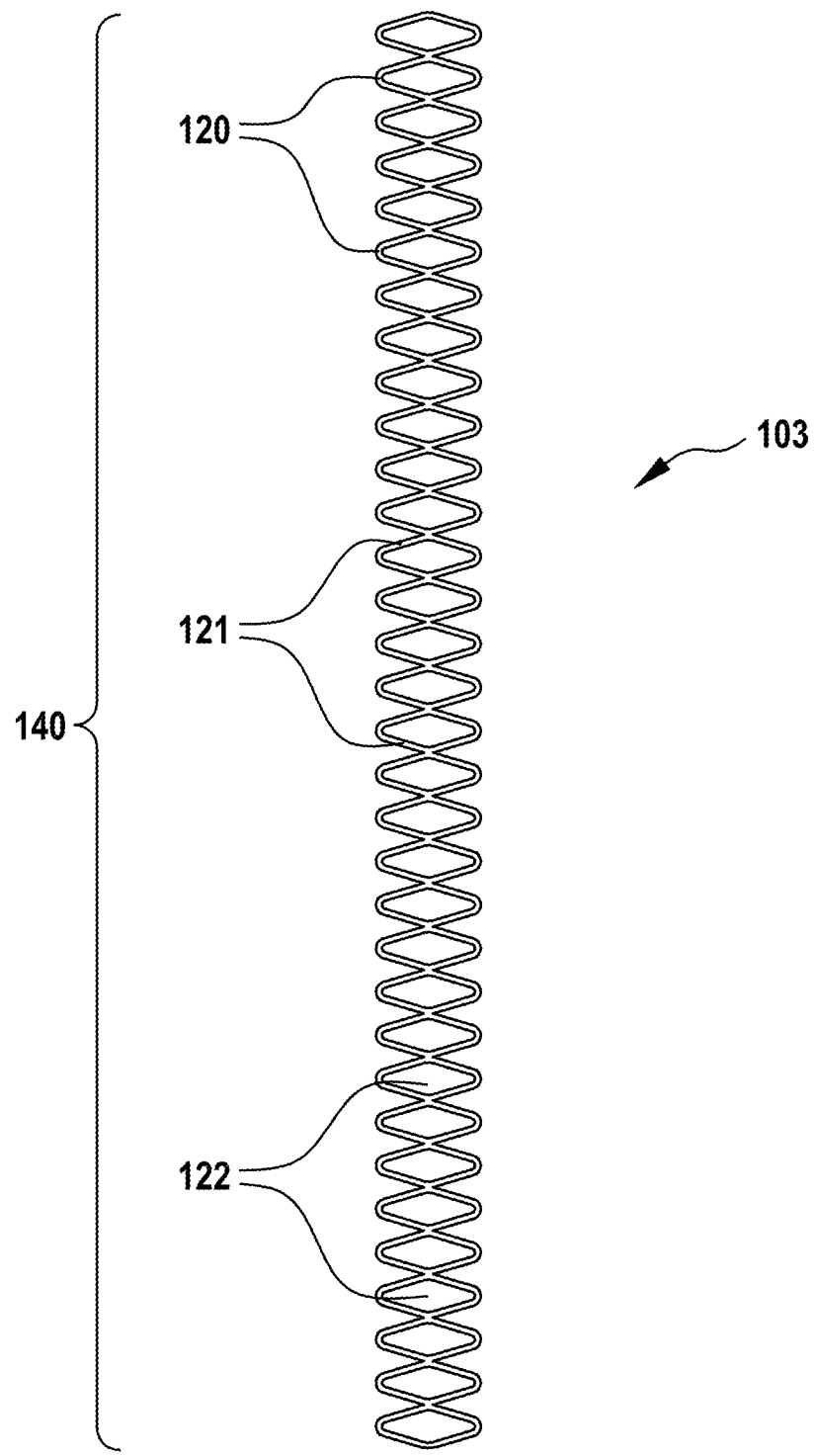
FIG. 4 shows an alternative embodiment of the stabilizing rod according to the invention.

FIG. 4 shows a further embodiment of the stabilizing rod 103 according to the invention. The stabilizing rod 103 consists only of the bending section 140, which in this case is formed only from a mesh belt structure 120. The mesh belt structure 120 is again formed from a mesh 121 which encloses rhombic gaps 122. The stabilizing rod 103 is bendable and light due to the mesh belt structure 120.

FIG. 5 shows different embodiments of the mesh belt structure 51, 52, 53, 54, 55, 56, 57, which can be used as an alternative to the rhombus structure shown in FIGS. 1 to 4. In each case, a segment with four structural elements is shown. In FIGS. 5A, 5B, 5C, and 5D, the structural elements are designed as triangles 60. The mesh belt structure 52, 53, 54 of FIGS. 5B, 5C, and 5D also has a thin bending rod 61, which is positioned differently in the three embodiments. In FIG. 5E, the structural elements of the mesh belt structure 55 are designed as circles 70. In FIG. 5F, the structural elements of the mesh belt structure 56 are designed as ovals 80, to which a thin bending rod 81 is again assigned. In FIG. 5G, the structural elements of the mesh belt structure 57 are designed as elongated curved bodies 90, to which a thin bending rod 91 is also assigned. The outer ends of the curved bodies 90 can bear against one another when the rod is bent and thus function as a stop limit.

The invention claimed is:

1. A stabilizing rod (99, 101) for an orthopedic aid (200), wherein the stabilizing rod (99, 101) consists essentially of plastic and comprises a bending section (140) having a mesh belt structure (120), wherein the stabilizing rod (99, 101) comprises a thin bending rod (150) and at least one mesh belt structure (120, 130) running on said thin bending rod, and wherein at least one end of the stabilizing rod (99, 101) has a gripping piece (111a, 111b), wherein the gripping piece comprises an eyelet or a knob on the stabilizing rod (99, 101), wherein a center region of the thin bending rod is offset relative to an inner edge of the at least one mesh belt structure (120, 130).

2. An orthopedic aid, comprising at least one stabilizing rod (99, 101) according to claim 1.

3. The orthopedic aid according to claim 2, wherein the orthopedic aid is a knee joint bandage (200).

4. The orthopedic aid according to claim 3, wherein the knee joint bandage (200) has two stabilizing rods (99, 101, 102) extending over a length of the knee joint bandage (200).

5. The orthopedic aid according to claim 4, wherein each of the bending sections (130) of the stabilizing rods (99, 101, 102) is located at least at a level of the knee (301) when the knee joint bandage (200) is in an applied state.

6. The stabilizing rod (101) according to claim 1, wherein the stabilizing rod (101) is formed from two mesh belt structures (120, 130).

7. The stabilizing rod (99, 101) according to claim 6, wherein the stabilizing rod (101) comprises a bending rod (150) running between the two mesh belt structures (120, 130).

8. The stabilizing rod (99, 101) according to claim 1, wherein the stabilizing rod (99, 101) is designed as one piece.

9. The stabilizing rod (99, 101) according to claim 1, wherein the mesh belt structure (120) extends over a length of the stabilizing rod (99, 101).

10. The stabilizing rod (99, 101) according to claim 1, wherein the thin bending rod (150) has a guide channel.

11. The stabilizing rod (99, 101) according to claim 1, wherein a single structural element of the at least one mesh belt structure (120, 130) has no more than four corners, and wherein the at least one mesh belt structure is triangular, circular, or rhomboid.

12. The stabilizing rod (99, 101) of claim 1, wherein an opening of the gripping piece and the thin bending rod (150) are formed as an integrated, one-piece material.

13. The stabilizing rod (99, 101) of claim 1, wherein the gripping piece comprises knobs.

14. A stabilizing rod (99, 101) for an orthopedic aid (200), wherein the stabilizing rod (99, 101) comprises a bending section (140) having a mesh belt structure (120) that is not comprised of flat-pressed coils of a helical spring, wherein the stabilizing rod (99, 101) comprises a thin bending rod, wherein a center region of the thin bending rod is offset relative to an inner edge of the mesh belt structure (120).

* * * * *